US012201996B2

(12) United States Patent
Chen et al.

(10) Patent No.: US 12,201,996 B2
(45) Date of Patent: Jan. 21, 2025

(54) PURIFYING DEVICE

(71) Applicant: GREE ELECTRIC APPLIANCES, INC. OF ZHUHAI, Guangdong (CN)

(72) Inventors: Huan Chen, Zhuhai (CN); Zhentao Hu, Zhuhai (CN); Yaozhen Lu, Zhuhai (CN); Xuedan Hou, Zhuhai (CN)

(73) Assignee: GREE ELECTRIC APPLIANCES, INC. OF ZHUHAI, Guangdong (CN)

( * ) Notice: Subject to any disclaimer, the term of this patent is extended or adjusted under 35 U.S.C. 154(b) by 368 days.

(21) Appl. No.: 17/766,469

(22) PCT Filed: Sep. 10, 2020

(86) PCT No.: PCT/CN2020/114349
§ 371 (c)(1),
(2) Date: Apr. 4, 2022

(87) PCT Pub. No.: WO2021/073324
PCT Pub. Date: Apr. 22, 2021

(65) Prior Publication Data
US 2023/0101583 A1    Mar. 30, 2023

(30) Foreign Application Priority Data

Oct. 17, 2019    (CN) .......................... 201910992209.3

(51) Int. Cl.
*B01D 53/32* (2006.01)
*B03C 3/36* (2006.01)
(Continued)

(52) U.S. Cl.
CPC .............. *B03C 3/86* (2013.01); *B01D 53/323* (2013.01); *B03C 3/361* (2013.01); *B03C 3/41* (2013.01); *B01D 2259/812* (2013.01)

(58) Field of Classification Search
CPC .. B01D 53/32; B03C 3/36; B03C 3/41; B03C 3/86
See application file for complete search history.

(56) References Cited

U.S. PATENT DOCUMENTS

| 5,847,514 A | 12/1998 | Dai |
| 2009/0078862 A1 | 3/2009 | Rodier et al. |
| 2018/0036677 A1* | 2/2018 | Bender ................ B01D 53/323 |

FOREIGN PATENT DOCUMENTS

| CN | 207134612 U | 3/2018 |
| CN | 108826407 A | 11/2018 |

(Continued)

OTHER PUBLICATIONS

Office Action dated Apr. 25, 2023 for Japanese Patent Application No. 2022-517841, including English translation (8 pages).

(Continued)

*Primary Examiner* — Sharon Pregler
(74) *Attorney, Agent, or Firm* — J. Miguel Hernandez; James R. Gourley; Carstens, Allen & Gourley, LLP

(57) ABSTRACT

A purifying device, including: an air guiding part provided with an air passage, a negative ion generator, and an air guiding cover. The negative ion generator includes an emitting head, and the emitting head is arranged to face the air passage. The air guiding part is provided with a first position limiting structure disposed on an inner wall of the air passage, and the first position limiting structure is provided with a position limiting groove configured to receive the emitting head. The air guiding cover is arranged on a top of the inner wall of the air passage and configured to press and cover the position limiting groove, and the inner wall of the air passage is configured to support the air guiding cover.

19 Claims, 5 Drawing Sheets

(51) Int. Cl.
*B03C 3/41* (2006.01)
*B03C 3/86* (2006.01)

(56) References Cited

FOREIGN PATENT DOCUMENTS

| | | |
|---|---|---|
| CN | 208296059 U | 12/2018 |
| CN | 208595584 U | 3/2019 |
| CN | 109967249 A | 7/2019 |
| CN | 110038401 A | 7/2019 |
| CN | 110639338 A | 1/2020 |
| CN | 210993652 U | 7/2020 |
| JP | 2004184004 A | 7/2004 |
| JP | 2013002416 A | 1/2013 |
| JP | 2014007028 A | 1/2014 |
| KR | 100757843 B1 | 9/2007 |
| KR | 1020140001330 A | 1/2014 |
| WO | 2011007597 A1 | 1/2011 |
| WO | 2019081580 A1 | 5/2019 |

OTHER PUBLICATIONS

Extended European Search Report for European Application No. 20877855.5 dated Aug. 31, 2022 (6 pages).

\* cited by examiner

PURIFYING DEVICE

CROSS-REFERENCE TO RELATED APPLICATION

This application is a U.S. National Stage of International Application No. PCT/CN2020/114349, filed on Sept. 10, 2020, entitled Purification Device and published as WO 2021/073324 A1 on Apr. 22, 2021, which claims priority of Chinese Patent Application No. 201910992209.3, filed with the CNIPA on Oct. 17, 2019, and entitled "Purifying Device", the disclosure of which is incorporated herein by reference in its entirety. Every patent application and publication listed in this paragraph is hereby incorporated by reference in its entirety, as an example.

TECHNICAL FIELD

The present disclosure relates to the technical field of household appliances, and particularly, to a purifying device.

BACKGROUND

An air purifier, also known as an "air cleaner", an air freshener, or a purifier, refers to a product capable of absorbing, decomposing, or transforming various air pollutants (generally including PM2.5, dust, pollen, peculiar smell, decoration pollution such as formaldehyde, bacteria, allergen, etc.) and effectively improving air cleanliness. Along with the serious air pollution and the improvement of people's living standards, the air purifier is becoming more and more popular.

The air cleaner in the related technology draws in air via a fan and purifies the air by filtering dust via a filter, which is called a passive adsorption and filtration-typed purifying principle, and the filter needs to be replaced regularly. However, the negative ion air purifier needs no consumptive material, and purifies the air, removes the dust, eliminates the peculiar smell, sterilizes, and actively captures harmful substances in the air only by means of negative ions produced by itself.

However, the negative ions need to be blown out by wind due to their short migration distances. If the negative ions are too far from the air outlet, they will be neutralized in the air before they come out of the purifier. When installed near the air outlet, the negative ion generating device often loosens and falls, which will affect the air purification efficiency of negative ions.

SUMMARY

Therefore, the technical problem to be solved by the present disclosure is to overcome a poor stability of a negative ion generator provided at an air outlet of an air cleaner in the related technology, and the present disclosure provides a purifying device.

The present disclosure provides a purifying device, including an air guiding part provided with an air passage, a negative ion generator, and an air guiding cover. The negative ion generator includes an emitting head. The emitting head is arranged to face the air passage. The air guiding part is provided with a first position limiting structure disposed on an inner wall of the air passage, and the first position limiting structure is provided with a position limiting groove configured to receive the emitting head.

The air guiding cover is arranged on a top of the inner wall of the air passage and configured to press and cover the position limiting groove, the inner wall of the air passage being configured to support the air guiding cover.

In some embodiments, the negative ion generator includes a negative ion high-voltage module, a negative ion generator, and connecting wires, a motor fixing frame is arranged at a center of the air guiding part, the negative ion high-voltage module is fixedly connected to the motor fixing frame by a threaded pole, and the connecting wires connect the negative ion high-voltage module with the negative ion generator, and are fixed on the motor fixing frame through a wire clamping buckle provided on the motor fixing frame.

In some embodiments, the negative ion generator is T-shaped, and is clamped on the inner wall of the air passage, the negative ion generator includes a lateral pole and a longitudinal pole, and the emitting head is arranged to protrude from a side of the lateral pole proximate to the air passage.

In some embodiments, the first position limiting structure includes at least one second protruding part that protrudes from an inner surface of the inner wall of the air passage, the second protruding part is provided with a bent portion extending upwards and is spaced apart from the inner wall of the air passage, and the longitudinal pole is configured to be limited in an area between the bent portion and the inner wall of the air passage.

In some embodiments, the first position limiting structure further includes auxiliary supporting parts, the auxiliary supporting parts are arranged at two sides of the second protruding part, and the auxiliary supporting parts are arranged in parallel with the second protruding part and configured to support the lateral pole.

In some embodiments, the auxiliary supporting parts are provided corresponding to the position limiting groove.

In some embodiments, a second position limiting structure is provided on the air guiding cover and disposed at a position corresponding to the first position limiting structure, and the second position limiting structure is configured to press and cover the position limiting groove.

In some embodiments, the second position limiting structure is a first protruding part arranged at a lower side of the air guiding cover and extending in a direction towards the lateral pole, and the first protruding part is configured to extend towards a central axis of the air guiding cover.

In some embodiments, air guiding blades are arranged in the air passage at even intervals, and the emitting head is arranged in a space between the air guiding blades.

In some embodiments, the purifying device is an air purifier.

The technical solutions of the present disclosure have the following advantages.

1. The present disclosure provides a purifying device, including an air guiding part provided with an air passage, a negative ion generator, and an air guiding cover. The negative ion generator includes an emitting head. The emitting head is arranged to face the air passage. A first position limiting structure is arranged on the air guiding part and disposed on an inner wall of the air passage, and the first position limiting structure is provided with a position limiting groove configured to receive the emitting head. The air guiding cover is arranged on a top of the inner wall of the air passage and configured to press and cover the position limiting groove, and the inner wall of the air passage is configured to support the air guiding cover.

Such an arrangement enables the negative ions produced by the negative ion generator to be blown out directly from the air passage, thus increasing the migration distance of the negative ions. Also, only the emitting head extends into the air passage and is concealingly arranged, thus having little effect on the air flow. The emitting head is arranged to be close to the air outlet, thus enabling a relatively large number of negative ions to be blown out, making the air flow smoother and the noise lower. In addition, the emitting head is positioned and installed by means of the position limiting groove on the first position limiting structure on the air guiding part, so that the emitting head is accurately installed on the inner wall of the air passage. In addition, by restricting other parts of the negative ion generator rather than the emitting head, the emitting head is prevented from falling out of the position limiting groove, thus ensuring the emitting head to be installed stably. Moreover, the air guiding cover presses and covers the inner wall of the air passage, thus fixing the emitting head at the installation position. The emitting head is restricted in different directions, thereby improving the installation stability of the negative ion generator installed on the inner wall of the air passage, overcoming the defect of the poor stability of the negative ion generator disposed at the air outlet in the related art. The present application has a simple structure and provides a convenient installation.

2. The negative ion generator provided by the present disclosure is T-shaped, and is clamped on the inner wall of the air passage, the negative ion generator includes a lateral pole and a longitudinal pole, and the emitting head is arranged to protrude from a side of the lateral pole proximate to the air passage.

On the one hand, such an arrangement makes it convenient for the emitting head to be restricted by means of the lateral pole after the emitting head is installed in the position limiting groove, thus ensuring that the emitting head will not fall out of the position limiting groove, and improving the fixation effect. The T-shaped negative ion generator makes it convenient for an operator to confirm a correct installation direction during the installation, and the purpose of limiting position may be achieved by fixing few parts. For example, by fixing the two sides of the lateral pole, the effect of restricting degrees of freedom in multiple directions may be achieved, thereby simplifying the arrangement of the limiting structure and reducing the cost.

3. The first position limiting structure provided by the present disclosure includes at least a second protruding part that protrudes from an inner surface of the inner wall of the air passage, the second protruding part is provided with a bent portion extending upwards and is spaced apart from the inner wall of the air passage, and the longitudinal pole is configured to be limited in an area between the bent portion and the inner wall of the air passage.

The second protruding part receives and supports the negative ion generator by configuring the bent portion, which is arranged on the inner surface of the inner wall of the air passage and extends upward, and stops the negative ion generator from moving away from the air guiding cover and the air passage.

4. The first position limiting structure provided by the present disclosure further includes auxiliary supporting parts, the auxiliary supporting parts are arranged at two sides of the second protruding part, and the auxiliary supporting parts are arranged in parallel with the second protruding part and configured to support the lateral pole.

In such an arrangement, the installation stability of the negative ion generator is improved by additionally arranging the receiving and supporting structure for the negative ion generator. Moreover, the auxiliary supporting parts are provided for the lateral pole, and configured to restrict the movement of the negative ion generator towards two sides of the lateral pole and fix the negative ion generator by cooperating with the second protruding part, the air guiding cover, and the inner wall of the air passage.

5. The second position limiting structure provided by the present disclosure is a first protruding part arranged at the lower side of the air guiding cover and extending in a direction towards the lateral pole, the first protruding part is configured to extend towards a central axis of the air guiding cover.

The air guiding cover is arranged at the top of the inner wall of the air passage, and configured to press and cover the position limiting groove to stop the emitting head of the negative ion generator from moving away from the air guiding part. The emitting head is arranged to protrude from the side of the lateral pole proximate to the air passage. The first protruding part is arranged at the lower side of the air guiding cover and configured to extend towards the central axis of the air guiding cover to subsidiarily restrict the lateral pole, thereby improving the stability of the fixing structure for the negative ion generator.

6. Air guiding blades are arranged in the air passage provided by the present disclosure at even intervals, and the emitting head is arranged in a space between the air guiding blades.

The air guiding blade are arranged in the air passage, thereby preventing the air from generating eddy currents in the air passage which will cause loss of energy, enabling the air flow to flow smoothly, and reducing the generation of noise.

DESCRIPTION OF THE DRAWINGS

In order to describe the embodiments of the present disclosure or the technical solutions in the related technology more clearly, the figures to be used in describing the embodiments or the related technology will be briefly described. Obviously, the figures to be described herein are merely some embodiments of the present disclosure. For those skilled in the art, other figures may be obtained according to these figures without involving any creative work.

DESCRIPTION OF REFERENCE SIGNS

Figure 1:
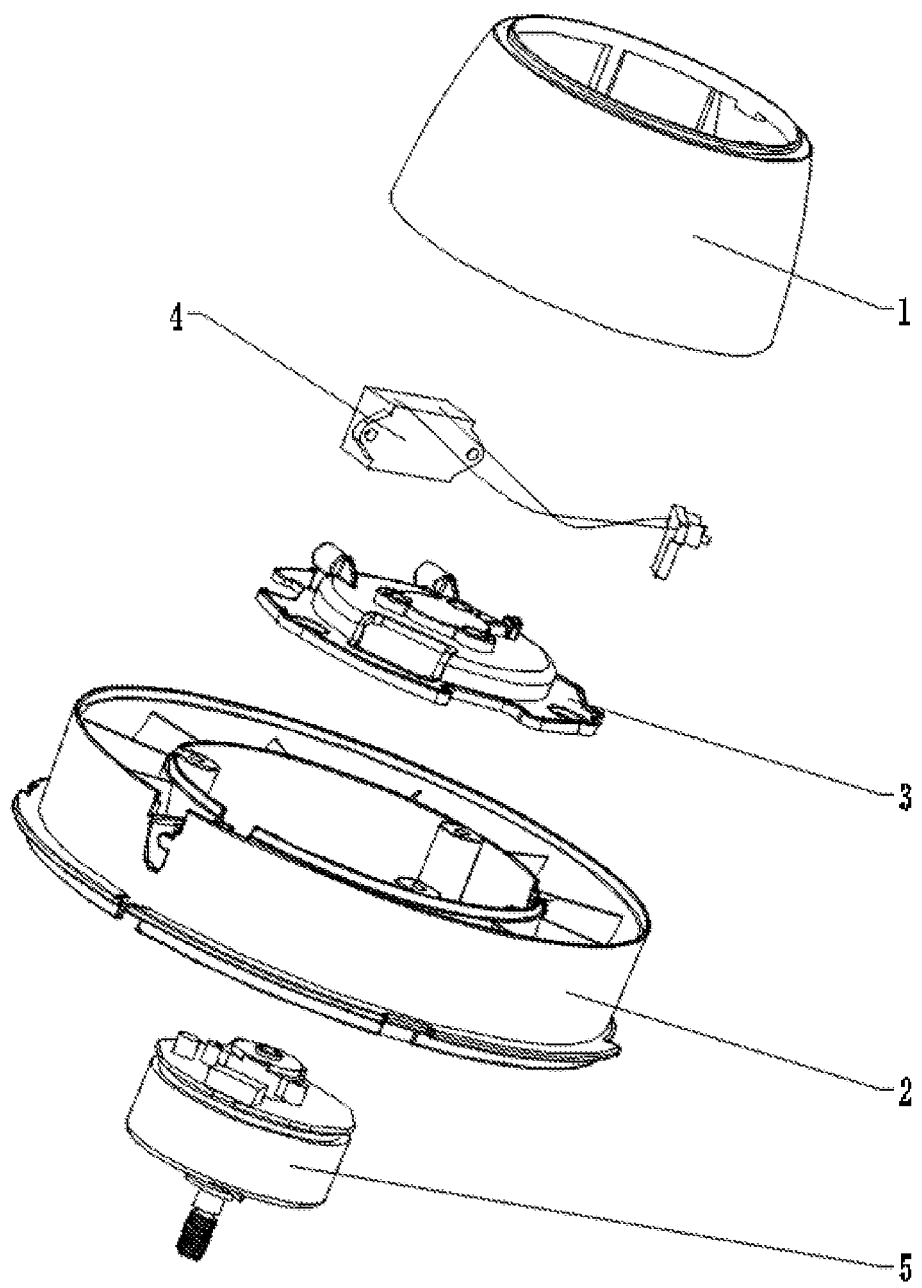
FIG. 1 is an exploded schematic view of part of a purifying device according to an embodiment of the present disclosure.

1—air guiding cover; 2—air guiding part; 3—motor fixing frame; 4—negative ion generator; 5—motor; 11—first protruding part; 21—inner wall of air passage; 22—position limiting groove; 23—second protruding part; 231—bent portion; 24—auxiliary supporting part; 25—air guiding blade; 31—threaded pole; 32—wire clamping buckle; 41—negative ion high-voltage module; 42—connecting wire; 43—negative ion generator; 431—emitting head; 432—lateral pole; 433—longitudinal pole.

DETAILED DESCRIPTION OF EMBODIMENTS

The technical solutions of the present disclosure will be clearly and completely described herein in conjunction with the accompanying drawings. Obviously, the described embodiments are part of the embodiments of the present disclosure, rather than all of the embodiments. Based on the embodiments in the present disclosure, all other embodiments obtained by those of ordinary skill in the art without creative work shall fall within the protection scope of the present disclosure.

In the description of the present disclosure, it should be noted that the terms "center", "upper", "lower", "left", "right", "vertical", "horizontal", "inner", "outer", etc., which indicate orientation or positional relationship based on the orientations or positional relationships shown in the drawings, are only used for the convenience of describing the present disclosure and simplifying the description, but do not indicate or imply that the indicated device or element must have a specific orientation or must be constructed or operated in a specific orientation. Therefore, these terms should not be construed as a limitation on the present disclosure. In addition, the terms "first", "second", and "third" are only used for the purpose of describing, but not be understood as indicating or implying relative importance.

In the description of the present disclosure, it should be noted that, unless otherwise clearly defined and limited, the terms "installation", "connection", and "communication" should be understood in a broad sense. For example, the connection may be a fixed connection, or a detachable connection, or an integral connection. The connection may be a mechanical connection or an electrical connection. The connection may be a direct connection, or an indirect connection through an intermediate medium, or may be an internal communication between two components. For those of ordinary skill in the art, the specific meanings of the above-mentioned terms in the present disclosure may be understood according to specific situations.

In addition, the technical features involved in different embodiments of the present disclosure described herein may be combined with each other as long as they do not conflict with each other.

Figure 2:
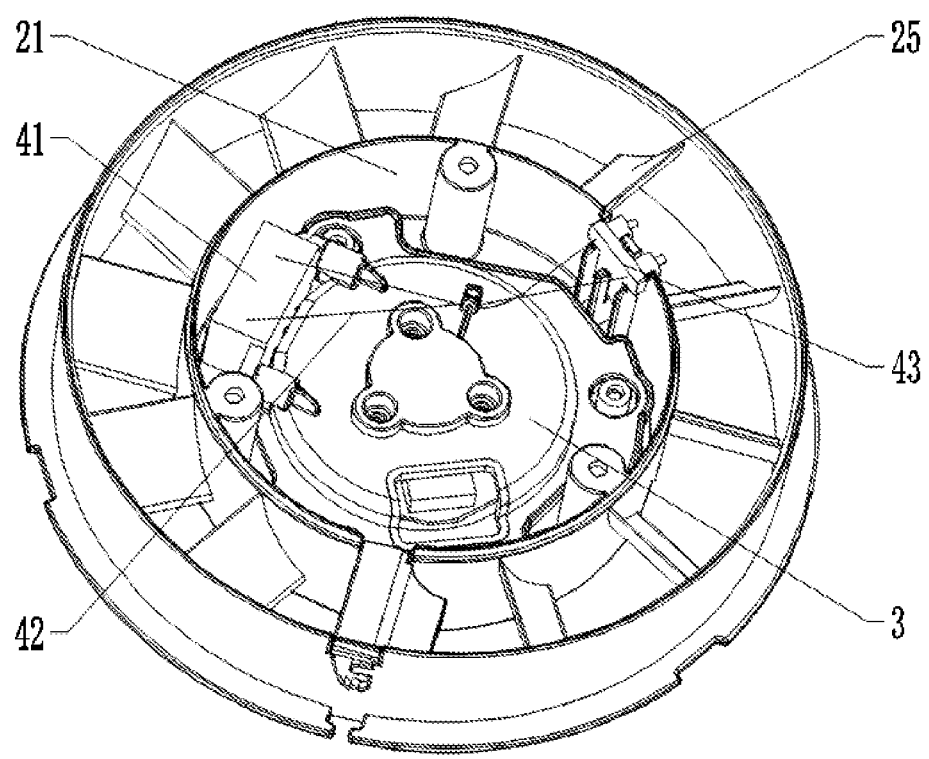
FIG. 2 is a 3D structural schematic view showing an air guiding part of the purifying device shown in FIG. 1.
Figure 3:
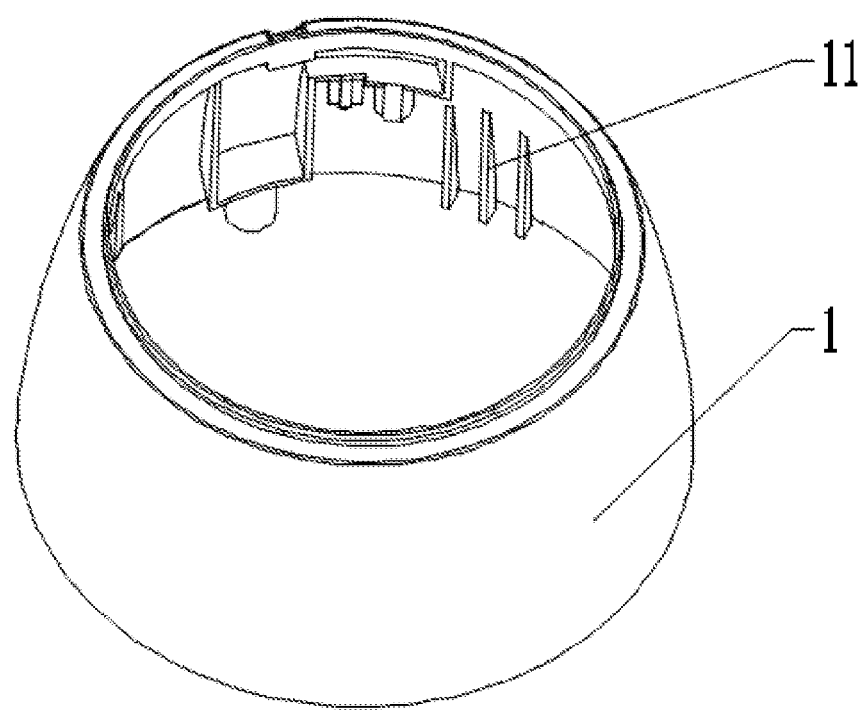
FIG. 3 is a 3D structural schematic view showing an air guiding cover of the purifying device shown in FIG. 1.
Figure 4:
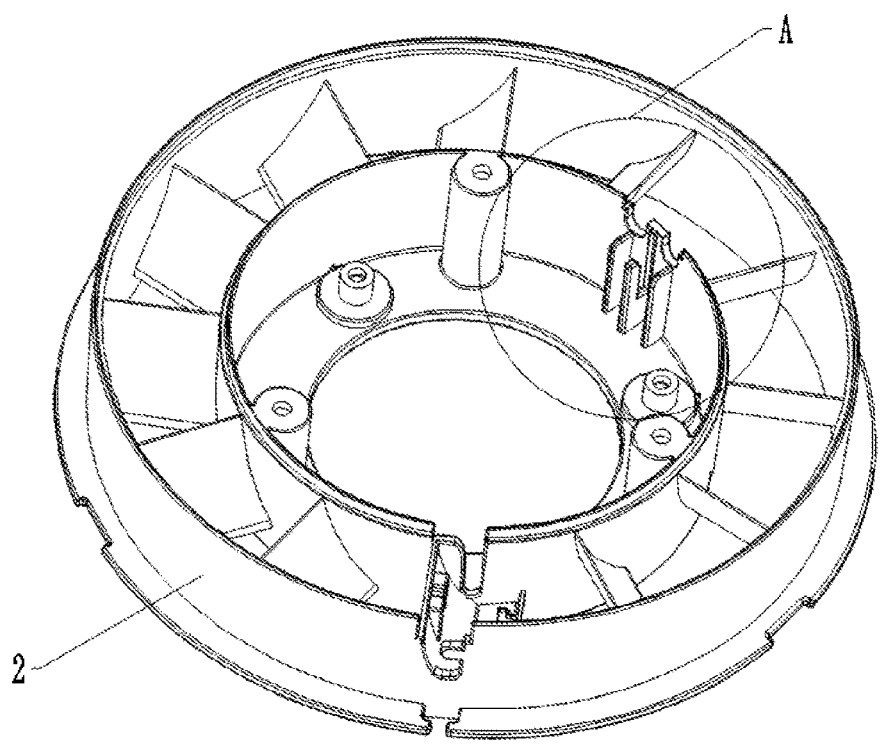
FIG. 4 is a 3D structural schematic view showing the air guiding part shown in FIG. 2 in a state that no motor fixing frame is installed.
Figure 5:
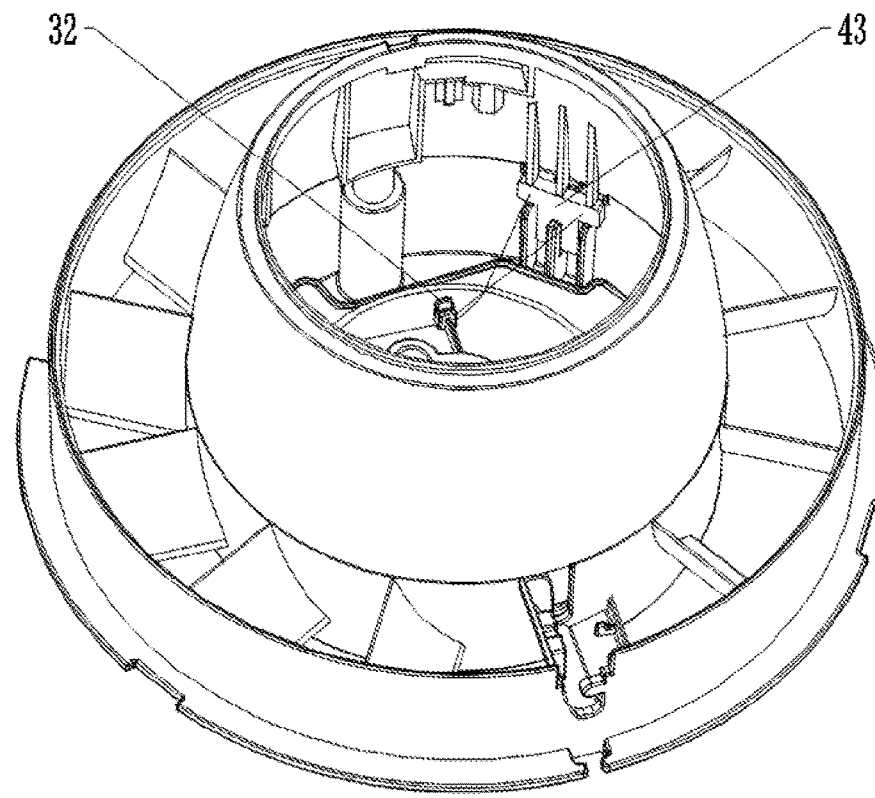
FIG. 5 is a 3D structural schematic view showing the air guiding part and the air guiding cover of the purifying device shown in FIG. 1 in a state of being installed and fixed.
Figure 6:
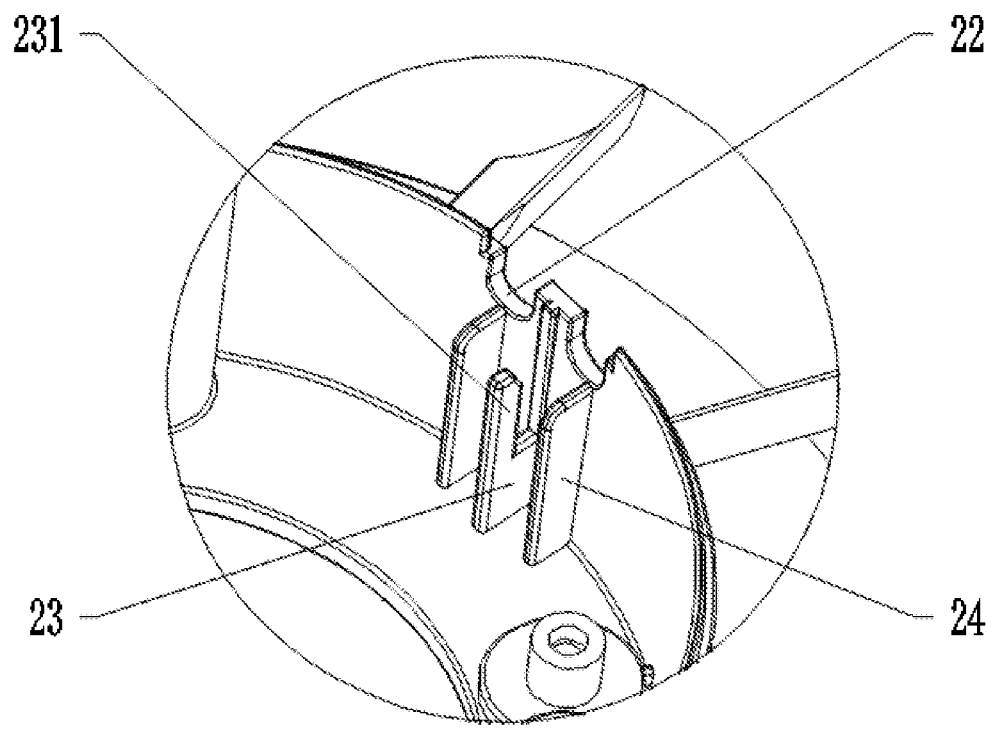
FIG. 6 is an enlarged structural schematic view showing part A of the air guiding part shown in FIG. 4 in the state that no motor fixing frame is installed.
Figure 7:
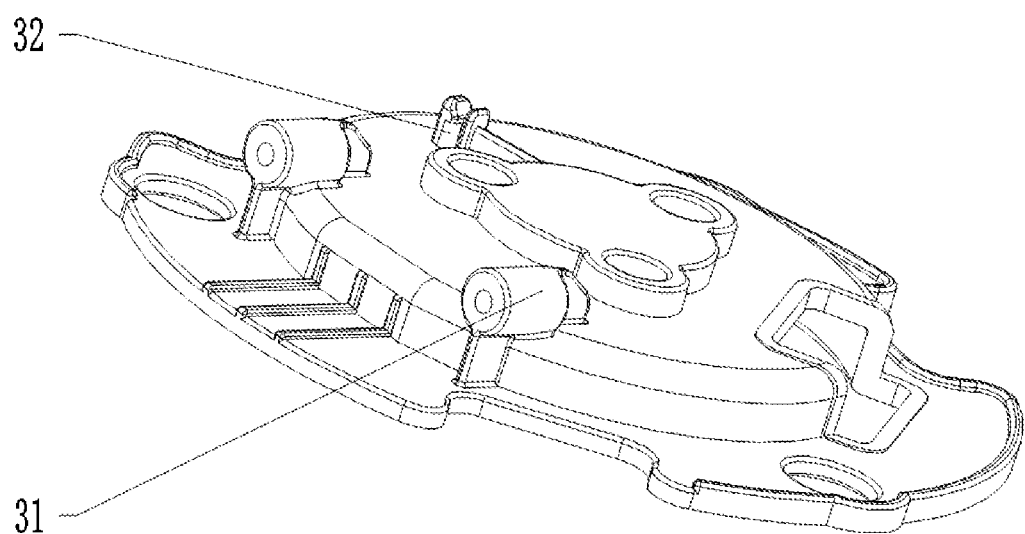
FIG. 7 is a 3D structural schematic view showing the motor fixing frame in the air guiding part shown in FIG. 2.
Figure 8:
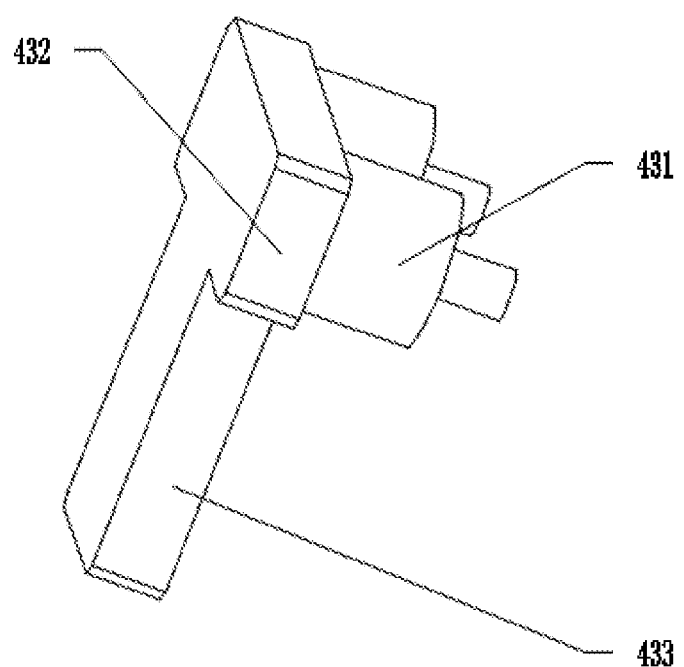
FIG. 8 is a 3D structural schematic view showing a negative ion generator shown in FIG. 1.

As shown in FIGS. 1 to 8, an embodiment provides a purifying device, including an air guiding part 2 provided with an air passage, a negative ion generator 4, and an air guiding cover 1. The negative ion generator 4 includes an emitting head 431. The emitting head 431 is arranged to face the air passage. The air guiding part 2 is provided with a first position limiting structure disposed on an inner wall 21 of the air passage. The first position limiting structure is provided with a position limiting groove 22 configured to receive the emitting head 431. The air guiding cover 1 is arranged on a top of the inner wall 21 of the air passage and configured to press and cover the position limiting groove 22. The inner wall 21 of the air passage is configured to support the air guiding cover 1.

Such an arrangement enables the negative ions produced by the negative ion generator 4 to be blown out directly from the air passage, thus increasing the migration distance of the negative ions. Moreover, only the emitting head 431 extends into the air passage and is arranged and installed concealingly, thus having little effect on the air flow. The emitting head 431 is arranged to be close to the air outlet, thus making a relatively large number of negative ions to be blown out, and resulting in a smoother air flow and a lower noise. In addition, the emitting head 431 is positioned and installed by means of the position limiting groove 22 on the first position limiting structure arranged on the air guiding part 2, so that the emitting head 431 is accurately installed on the inner wall 21 of the air passage. In addition, by restricting other part of the negative ion generator 4 rather than the emitting head 431, the emitting head 431 is prevented from disengaging from the position limiting groove 22, thus ensuring the emitting head 431 to be installed stably. Moreover, the air guiding cover 1 presses and covers the inner wall 21 of the air passage, thus fixing the emitting head 431 at the installation position. The emitting head 431 is restricted in different directions, thereby improving the installation stability of the negative ion generator 4 installed on the inner wall 21 of the air passage, overcoming the defect of the poor stability of the negative ion generator 4 disposed at the air outlet in the related art. The present application has a simple structure and provides a convenient installation.

In this embodiment, the air passage is annular and arranged along an outer edge of the air guiding part 2. The position limiting groove 22 has a double-groove structure adapted for installation of the cylindrical emitting head 431. A lower end of the air guiding cover 1 engages with the inner wall 21 of the air passage, and the air guiding cover 1 and the air guiding part 2 may be connected by a detachable threaded pole 31. The purifying device is an air purifier.

The negative ion generator 4 includes a negative ion high-voltage module 41, a negative ion generator 43 and connecting wires 42. A motor fixing frame 3 is arranged at the center of the air guiding part 2. The negative ion high-voltage module 41 is fixedly connected to the motor fixing frame 3 by means of the threaded pole 31. The connecting wires 42 connect the negative ion high-voltage module 41 with the negative ion generator 43, and are fixed on the motor fixing frame 3 by the wire clamping buckle 32 provided on the motor fixing frame 3. In this embodiment, a motor 5 is fixed on one side of the motor fixing frame 3, and the negative ion generator 4 is fixed on another side of the motor fixing frame 3. The motor fixing frame 3 is detachable, and the negative ion high-voltage module 41 is fixed on the motor fixing frame 3 by means of two threaded poles 31. Two connecting wires 42 are provided and connected to and clamped in the wire clamping buckle 32 disposed at the center of the motor fixing frame 3. The negative ion generator 43 is arranged on a side of the inner wall 21 of the air passage proximate to the air guiding cover 1.

As an alternative implementation, the wire clamping buckle 32 may be omitted, and the negative ion high-voltage module 41 may be fixed on the inner wall 21 of the air passage.

The negative ion generator 43 is T-shaped, and is clamped on the inner wall 21 of the air passage. The negative ion generator 43 includes a lateral pole 432 and a longitudinal pole 433. The emitting head 431 is arranged to protrude from a side of the lateral pole 432 proximate to the air passage.

On the one hand, such an arrangement makes it convenient for the emitting head 431 to be restricted by means of the lateral pole 432 after the emitting head 431 is installed in the position limiting groove 22, thus ensuring that the emitting head 431 will not fall out of the position limiting groove 22, and improving the fixation effect. The T-shaped negative ion generator 43 makes it convenient for an operator to confirm a correct installation direction during the installation, and the purpose of limiting position may be achieved by fixing fewer parts. For example, by fixing the two sides of the lateral pole 432, the effect of restricting degrees of freedom in multiple directions may be achieved, thereby simplifying the arrangement of the limiting structure and reducing the cost.

As an alternative embodiment, the negative ion generator 43 may be configured to be square or cylindrical.

The first position limiting structure includes a second protruding part 23 that protrudes from an inner surface of the inner wall 21 of the air passage. The second protruding part 23 is provided with a bent portion 231 extending upwards and is spaced apart from the inner wall 21 of the air passage. The longitudinal pole 433 is configured to be limited in the area between the bent portion 231 and the inner wall 21 of the air passage. The second protruding part 23 receives and supports the negative ion generator 43 by configuring the bent portion 231, which protrudes from the inner surface of the inner wall 21 of the air passage and extends upward, and stops the negative ion generator 43 from moving away from the air guiding cover 1 and the air passage. In this embodiment, the second protruding part 23 is in a shape of a sheet, and a distance between the bent portion 231 and the inner wall 21 of the air passage is equal to the thickness of the longitudinal pole 433, which is a distance between two sides of the longitudinal pole 433 facing the air passage and away from the air passage, respectively.

As an alternative embodiment, a plurality of groups of second protruding parts 23 may be provided, and the distance between the bent portion 231 and the inner wall 21 of the air passage may be greater than the thickness of the longitudinal pole 433.

The first position limiting structure further includes auxiliary supporting parts 24. The auxiliary supporting parts 24 are arranged at two sides of the second protruding part 23. The auxiliary supporting parts 24 are arranged in parallel with the second protruding part 23 and configured to support the lateral pole 432. In such an arrangement, the installation stability of the negative ion generator 43 is improved by additionally arranging the receiving and supporting structure for the negative ion generator 43. Moreover, the auxiliary supporting parts 24 are provided for the lateral pole 432, and configured to restrict the movement of the negative ion generator 43 towards two sides of the lateral pole 432 and fix the negative ion generator 43 by cooperating with the second protruding part 23, the air guiding cover 1, and the inner wall 21 of the air passage. In this embodiment, the auxiliary supporting part 24 is a rectangular sheet. Two auxiliary supporting parts 24 are provided, and the space therebetween is equal to a width between two sides of the longitudinal pole 433 proximate to the auxiliary supporting parts 24 respectively.

The auxiliary supporting parts 24 are provided corresponding to the position limiting groove 22. A second position limiting structure is provided on a position of the air guiding cover 1 corresponding to the first position limiting structure. The second position limiting structure is configured to press and cover the position limiting groove 22. The second position limiting structure is a first protruding part 11 arranged at the lower side of the air guiding cover 1 and extending in a direction towards the lateral pole 432. The first protruding part 11 is further configured to extend towards the central axis of the air guiding cover 1. In this embodiment, a protruding height of the first protruding part 11 gradually increases in a direction towards the air guiding part 2. As an alternative embodiment, the protruding height of the first protruding part 11 does not change in the direction towards the air guiding part 2.

The air guiding cover 1 is arranged at the top of the inner wall 21 of the air passage, and presses and covers the position limiting groove 22 to stop the emitting head 431 of the negative ion generator 43 from moving away from the air guiding part 2. The emitting head 431 is arranged to protrude from the side of the lateral pole 432 proximate to the air passage. The first protruding part 11 is arranged at the lower side of the air guiding cover 1 and extends towards the central axis of the air guiding cover 1 to subsidiarily restrict the lateral pole 432, thereby improving the stability of the fixing structure for the negative ion generator 43.

As an alternative embodiment, the auxiliary supporting part 24, the first protruding part 11, and the second protruding part 23 may be block-shaped or the like.

The air guiding blades 25 are arranged in the air passage at even intervals, and the emitting head 431 is arranged in a space between the air guiding blades 25. The air guiding blade 25 are arranged in the air passage, thereby preventing the air from generating eddy currents in the air passage which will cause loss of energy, enabling the air flow to flow smoothly, and reducing the generation of noise. As an alternative embodiment, the air guiding blades 25 may be omitted.

Obviously, the examples above are merely used for clear description of the embodiments, but not intended to limit the embodiments. For those of ordinary skill in the art, various variations or changes may be made on the basis of the above description. It is unnecessary and impossible to illustrate all embodiments herein. The various variations or changes obtained from these embodiments are still within the scope of the protection of the present disclosure.

What is claimed is:

1. A purifying device, comprising:
   an air guiding part provided with an air passage;
   a negative ion generator, wherein: the negative ion generator comprises an emitting head; the emitting head is arranged to face the air passage; the air guiding part is provided with a first position limiting structure disposed on an inner wall of the air passage; and the first position limiting structure is provided with a position limiting groove configured to receive the emitting head; and
   an air guiding cover, arranged on a top of the inner wall of the air passage and configured to press and cover the position limiting groove, the inner wall of the air passage being configured to support the air guiding cover;
   wherein the negative ion generator further comprises a negative ion high-voltage module, a negative ion generator, and connecting wires;
   a motor fixing frame is arranged at a center of the air guiding part;
   a negative ion high-voltage module is fixedly connected to the motor fixing frame by a threaded pole; and
   the connecting wires connect the negative ion high-voltage module with the negative ion generator, and are fixed on the motor fixing frame through a wire clamping buckle provided on the motor fixing frame.

2. The purifying device according to claim 1, wherein:
   the negative ion generator is T-shaped, and is clamped on the inner wall of the air passage;
   the negative ion generator comprises a lateral pole and a longitudinal pole; and the emitting head is arranged to protrude from a side of the lateral pole proximate to the air passage.

3. The purifying device according to claim 2, wherein:
the first position limiting structure comprises at least one second protruding part that protrudes from an inner surface the inner wall of the air passage;
the at least one second protruding part is provided with a bent portion extending upwards and is spaced apart from the inner wall of the air passage; and
the longitudinal pole is configured to be limited in an area between the bent portion and the inner wall of the air passage.

4. The purifying device according to claim 3, wherein:
the first position limiting structure further comprises auxiliary supporting parts;
the auxiliary supporting parts are arranged at two sides of the second protruding part; and
the auxiliary supporting parts are arranged in parallel with the second protruding part and configured to support the lateral pole.

5. The purifying device according to claim 4, wherein the auxiliary supporting parts are provided corresponding to the position limiting groove.

6. The purifying device according to claim 1, wherein:
a second position limiting structure is provided on the air guiding cover and disposed at a position corresponding to the first position limiting structure; and
the second position limiting structure is configured to press and cover the position limiting groove.

7. The purifying device according to claim 6, wherein:
the second position limiting structure includes a first protruding part, arranged at a lower side of the air guiding cover and extending in a direction towards a lateral pole of the negative ion generator of the negative ion generator, the first protruding part (11) is further configured to extend towards a central axis of the air guiding cover.

8. The purifying device according to claim 1, wherein:
air guiding blades are arranged in the air passage at even intervals; and
the emitting head is arranged in a space between the air guiding blades.

9. The purifying device according to claim 1, wherein the purifying device is an air purifier.

10. The purifying device according to claim 1, wherein the air passage is annular and arranged along an outer edge of the air guiding part.

11. The purifying device according to claim 1, wherein the position limiting groove has a double-groove structure adapted for installation of a cylindrical emitting head.

12. The purifying device according to claim 1, wherein a lower end of the air guiding cover is configured to engage with the inner wall of the air passage, and the air guiding cover and the air guiding part are connected by a detachable threaded pole.

13. The purifying device according to claim 1, wherein a motor is fixed on one side of the motor fixing frame, and the negative ion generator is fixed on another side of the motor fixing frame.

14. The purifying device according to claim 1, wherein two connecting wires are provided and connected to and clamped in the wire clamping buckle disposed at a center of the motor fixing frame, and the negative ion generator is arranged on a side of the inner wall of the air passage proximate to the air guiding cover.

15. The purifying device according to claim 1, wherein the negative ion generator is square or cylindrical.

16. The purifying device according to claim 3, wherein the at least one second protruding part is in a shape of a sheet, and a distance between the bent portion and the inner wall of the air passage is equal to a thickness of the longitudinal pole, the thickness of the longitudinal pole is a distance a distance between two sides of the longitudinal pole facing the air passage and away from the air passage, respectively.

17. The purifying device according to claim 3, wherein a plurality of groups of second protruding parts are provided, and a distance between the bent portion and the inner wall of the air passage is greater than a thickness of the longitudinal pole, the thickness of the longitudinal pole is a distance a distance between two sides of the longitudinal pole facing the air passage and away from the air passage, respectively.

18. The purifying device according to claim 7, wherein a protruding height of the first protruding part gradually increases in a direction towards the air guiding part.

19. The purifying device according to claim 7, wherein an auxiliary supporting part of the first position limiting structure, the first protruding part, and a second protruding part of the first position limiting structure are block-shaped.

* * * * *